(12) United States Patent
Neuman et al.

(10) Patent No.: US 9,327,115 B2
(45) Date of Patent: May 3, 2016

(54) IMPLANT DEVICE FOR STIMULATING OSTEOGENESIS AND OSSEOINTEGRATION

(75) Inventors: Moshe Neuman, Ramat-Gan (IL); Joseph Shechter, Holon (IL)

(73) Assignee: Magdent Ltd., Ramat-Gan (IL)

( * ) Notice: Subject to any disclaimer, the term of this patent is extended or adjusted under 35 U.S.C. 154(b) by 0 days.

(21) Appl. No.: 13/503,854

(22) PCT Filed: Oct. 28, 2010

(86) PCT No.: PCT/IL2010/000897
§ 371 (c)(1),
(2), (4) Date: Apr. 25, 2012

(87) PCT Pub. No.: WO2011/051947
PCT Pub. Date: May 5, 2011

(65) Prior Publication Data
US 2012/0215281 A1    Aug. 23, 2012

Related U.S. Application Data

(60) Provisional application No. 61/255,904, filed on Oct. 29, 2009.

(51) Int. Cl.
*A61B 18/18* (2006.01)
*A61N 1/32* (2006.01)
*A61N 2/02* (2006.01)

(52) U.S. Cl.
CPC . *A61N 1/326* (2013.01); *A61N 2/02* (2013.01)

(58) Field of Classification Search
CPC ............. A61N 2/02; A61N 1/40; A61N 1/32; A61N 1/326; A61N 1/36146; A61N 1/05; A61N 2005/0626; A61N 1/08; A61N 1/0502; A61N 1/3718; A61N 1/205; A61F 2250/0001; A61B 2017/564; A61B 2018/00642; A61B 17/68; A61B 17/7016; A61B 17/88; A61B 5/0031

USPC .............. 607/1–2, 50–52, 100, 115–116, 139
See application file for complete search history.

(56) References Cited

U.S. PATENT DOCUMENTS

| | | | | |
|---|---|---|---|---|
| 3,893,462 A | * | 7/1975 | Manning ................... | A61N 1/40 600/13 |
| 4,315,503 A | * | 2/1982 | Ryaby et al. ..................... | 600/14 |

(Continued)

FOREIGN PATENT DOCUMENTS

| | | |
|---|---|---|
| WO | WO 2009/019688 | 2/2009 |
| WO | WO 2011/051947 | 5/2011 |
| WO | WO 2013/164824 | 11/2013 |

OTHER PUBLICATIONS

International Search Report and the Written Opinion Dated Aug. 12, 2013 From the International Searching Authority Re. Application No. PCT/IL2013/050370.

(Continued)

*Primary Examiner* — Deborah Malamud

(57) ABSTRACT

An implant device for stimulating osteogenesis and osseointegration comprises a hollow annular housing member, a pulsed current modulator, and a coil connected to the current modulator. The current modulator and at least a portion of the coil are mounted within the housing member. A frequency of the pulsed current is selected to generate an electromagnetic field of a predetermined flux density that penetrates, and propagates radially outwardly from, the housing member for a sufficiently large propagation distance to stimulate osteogenesis and osseointegration, by means of the generated electromagnetic field, of a bone region in which the implant device is implanted and which is disposed radially outwardly from the housing member.

58 Claims, 14 Drawing Sheets

(56) References Cited

U.S. PATENT DOCUMENTS

| | | | |
|---|---|---|---|
| 5,292,252 | A | 3/1994 | Nickerson et al. |
| 6,032,677 | A | 3/2000 | Blechman et al. |
| 6,034,295 | A | 3/2000 | Rehberg et al. |
| 6,605,089 | B1 | 8/2003 | Michelson |
| 2004/0176805 | A1 | 9/2004 | Whelan et al. |
| 2006/0265026 | A1 | 11/2006 | Madjar et al. |
| 2015/0094521 | A1 | 4/2015 | Neuman et al. |

OTHER PUBLICATIONS

Shupak et al. "Therapeutic Uses of Pulsed Magnetic-Field Exposure: A Review", The Radio Science Bulletin, 307: 9-32, Dec. 2003. p. 10.

International Search Report and the Written Opinion Dated Mar. 15, 2011 From the International Searching Authority Re. Application No. PCT/IL2010/000897.

Matsumoto et al. "Pulsed Electromagnetic Fields Promote Bone Formation Around Dental Implants Inserted Into the Femur of Rabbits", Clinical Oral Implants Research, 11: 354-360, 2000. Abstract, Table 1, p. 357, col. 1, Para 1, col. 2, Para 3—p. 358, col. 2, Para 5.

Supplementary European Search Report and the European Search Opinion Dated Oct. 14, 2013 From the European Patent Office Re. Application No. 10826227.0.

Matsumoto et al. "Pulsed Electromagnetic Fields Promote Bone Formation Around Dental Implants Inserted Into the Femur of Rabbits", Clinical Oral Implants Research, XP008155161, 11(4): 354-360, Jan. 1, 2000.

Communication Pursuant to Article 94(3) EPC Dated May 30, 2014 From the European Patent Office Re. Application No. 10826227.0.

International Preliminary Report on Patentability Dated Nov. 13, 2014 From the International Bureau of WIPO Re. Application No. PCT/IL2013/050370.

Barak et al. "A New Device for Improving Dental Implants Anchorage: A Histological and Micro-Computed Tomography Study in the Rabbit", Clinical Oral Implants Research, 00: 1-8, First Published Aug. 6, 2015.

Matsumoto et al. "Pulsed Electromagnetic Fields Promote Bone Formation Around Dental Implants Inserted Into Femur of Rabbits", Clinical Oral Implants Research, 11(4): 354-360, Aug. 2000.

Ozen et al. "Evaluation of Pulsed Electromagnetic Fields on Bone Heafing After Implant Placement in the Rabbit Mandibular Model", Turkish Journal of Medical Sciences, 34(2): 91-95, 2004.

\* cited by examiner

IMPLANT DEVICE FOR STIMULATING OSTEOGENESIS AND OSSEOINTEGRATION

RELATED APPLICATIONS

This application is a National Phase of PCT Patent Application No. PCT/IL2010/000897 having International filing date of Oct. 28, 2010, which claims the benefit of priority of U.S. Provisional Patent Application No. 61/255,904 filed on Oct. 29, 2009. The contents of the above applications are all incorporated herein by reference.

FIELD OF THE INVENTION

The present invention relates to the field of implant devices. More particularly, the present invention relates to an implant device for stimulating osteogenesis and osseointegration.

BACKGROUND OF THE INVENTION

Endosseous root form implants are devices that are mainly used for support of dental prosthetic pieces. They can be also used for the anchorage of orthodontic devices.

Prior art dental implant treatments suffer from the following limitations: (1) Duration of Treatment—the treatment has a long healing period, after implant placement and before teeth restoration of: 3-4 months in the lower jaw, 4-6 months in the upper jaw, and 6-9 months for bone graft cases such as ridge augmentation and sinus lift; (2) The implantation failure rate is higher with respect to those suffering from osteoporosis, or reduced bone mass and density, due to a low degree of osseointegration. An implant is generally considered to be osseointegrated when it contacts the adjacent bone without any progressive relative movement therebetween. It is estimated that 20% of potential implantees for dental implantation suffer from this problem, this value constantly increasing due to the wordlwide population increase of elderly people; (3) An implantation cannot be performed when there is not enough available bone at the implantation site. It is estimated that 30% of potential implantees for dental implantation suffer from this problem. These patients have to undergo bone graft procedures such as ridge augmentation and sinus lift.

It would therefore be desirable to provide an implant device for stimulating osteogenesis, or bone development, and to thereby increase the implantation success rate as well as to shorten the treatment duration during which the bone-forming cells and the bone tissue surrounding the implant sufficiently develop and become osseointegrated.

The use of electric and electromagnetic fields to stimulate biologic systems has received attention in medicine. In the field of orthopedics, a pulsed electromagnetic field (PEMF) has been successfully used to induce healing in fractures of human long bones that proved resistant to conventional treatment and frequently required amputation. [Ryaby, J. T. (1998), "Clinical Effects of Electromagnetic and Electric Fields on Fracture Healing", Clinical Orthopedics and Related Research 355: 205-215] Applied electrical and electromagnetic fields can alter the normal electrical states of bone and cartilage, induce increased rates of cellular division and metabolism, and thus promote increased healing of bony and cartilage defects.

Muscle, ligament, bone, cartilage, blood, and adult stem-cell production all respond to electric and electromagnetic fields, and these biophysical field agents can be applied in therapeutic contexts. Electric and electromagnetic fields regulate extra-cellular matrix synthesis and stimulate repair of fractures and nonunions. Studies of electric and electromagnetic fields suggest they (1) regulate proteoglycan and collagen synthesis and increase bone formation in models of endochondral ossification, (2) accelerate bone formation and repair, (3) increase union rates in fractures previously refractory to healing, and (4) produce results equivalent to bone grafts. Electric and electromagnetic fields regulate the expression of genes in connective tissue cells for extra-cellular matrix proteins, which results in an increase in cartilage and bone. They also increase gene expression for and synthesis of growth factors, which may be an intermediary mechanism of activity and may amplify field effects through autocrine and paracrine signaling.

However, electromagnetic fields have not been used heretofore to stimulate osteogenesis and osseointegration with respect to dental implants. Dental implants are anchored into the jaw bone, and the entire circumference of an implant has to be osseointegrated with the jaw bone, requiring a long treatment duration as described hereinabove. An electromagnetic treatment to effectively stimulate osseointegration in dental implants therefore has to be ongoing, and an ambulatory treatment whereby a dental implantee is irradiated at a clinic by an electromagnetic field during a limited number of sessions per week will not be efficacious.

An electromagnetic treatment is energy intensive, and an electromagnetic field generator carried by the implantee and in constant use needs to be constantly recharged. Due to the need of constant recharging, an electromagnetic field generator cannot be conveniently localized within the oral cavity.

U.S. Pat. No. 5,292,252 to Nickerson et al discloses a stimulator healing cap for enhancing in a patient the growth of bone cells and bone tissue surrounding a dental implant. The stimulator healing cap includes a top cap portion containing a direct current source, and a threaded portion which attaches to the implant in the same way as a cover screw. In one embodiment, the current source is coupled to a coil which surrounds a longitudinal core creating an electromagnetic field around the implant and thus in the surrounding bone tissue.

The electromagnetic field that is generated by the current source is a static magnetic field (SMF), and the stimulation of bone growth by a SMF has not yet been definitively established. Another disadvantage of this healing cap is that the constantly operating battery that can be housed within its small internal volume is of an insufficient capacity for the required healing period.

U.S. Pat. No. 6,034,295 to Rehberg et al discloses an implantable device, including a dental implant, formed with an internal cavity into which the bone tissue that surrounds the implanted device is intended to grow. The device is provided with at least two electrodes, one of which is located within the cavity and spaced apart from the inside of the body that forms the cavity, and a second electrode when the body is made of an electrically conductive material, which together with the internal electrode, forms a kind of coaxial structure for generating a low-frequency alternating current for promoting tissue growth. However, an electric field generated by electrodes will not propagate beyond the outermost electrode, and is therefore incapable of stimulating osteogenesis in damaged or osteoporotic tissue outwardly spaced from the implant.

It is an object of the present invention to provide a dental implant device for stimulating osteogenesis.

It is an additional object of the present invention to provide a dental implant device for stimulating osseointegration.

It is an additional object of the present invention to provide a dental implant device for effectively stimulating osteogenesis by means of a pulsed electromagnetic field.

It is an additional object of the present invention to provide a dental implant device for stimulating osteogenesis which does not require a battery for powering the device to be replaced or recharged.

Other objects and advantages of the invention will become apparent as the description proceeds.

SUMMARY OF THE INVENTION

The present invention is an implant device that generates electromagnetic fields for biologic effects such as tissue repair and bone formation, serving as a therapeutic mechanism.

The implant device for stimulating osteogenesis and osseointegration, comprises a hollow annular housing member, a pulsed current modulator, and a coil connected to said current modulator, said current modulator and at least a portion of said coil being mounted within said housing member, wherein a frequency of said pulsed current is selected to generate an electromagnetic field of a predetermined flux density that penetrates, and propagates radially outwardly from, said housing member for a sufficiently large propagation distance to stimulate osteogenesis, and osseointegration by means of said generated electromagnetic field, of a bone region in which said implant device is implanted and which is disposed radially outwardly from said housing member.

An outer surface of the housing member is sufficiently electrically charged by means of the generated electromagnetic field to stimulate osseointegration with an adjacent bone region.

In one aspect, each pulse that is generated by the current modulator is of a sufficient duration to ensure that the total accumulated amount of energy associated with the electromagnetic field that is absorbed during a predetermined period by the bone region is greater than a predetermined amount.

In one aspect, the hollow housing member is engageable with an implanted root.

In one aspect, the housing member is a healing abutment engageable with an implanted root.

In one aspect, the hollow housing member is an implantable root.

As referred to herein, the following terms refer to the corresponding relative location of elements of the implant device when employed as a dental implant device, the relative locations also being applicable when employed as a different type of implant device:
  "cervical"—along a line between the upper and lower jaws, and more particularly, along a line between the implant root and a covering of the implant device;
  "coronal"—along a cervical line, toward the implant device covering;
  "apical"—along a cervical line, toward the implant root; and
  "radial"—along a line generally coinciding with the radius of the substantially circular implant device, or along a line parallel to a line generally coinciding with the radius of the substantially circular implant device, and substantially perpendicular to a cervical line.

In one aspect, the coil comprises a first portion disposed within a first housing member element and a second portion disposed within a second housing member element.

In one aspect, the coil is a continuous coil that is formed with one or more windings.

In one aspect, the first housing member element is a coronal cap and the second housing member element is a hollow screw, a coronal end of said hollow screw being threadedly engageable with said cap and an apical end of said hollow screw being threadedly engageable with an implanted root.

In one aspect, the coil is a frame coil.

In one aspect, the first portion of each loop of the frame coil has a width substantially equal to the width of the first housing member element and the second portion of each loop of the frame coil has a width substantially equal to the width of the second housing member element.

In one aspect, the frame coil comprises a plurality of aligned loops.

In one aspect, the frame coil comprises two sections that are substantially mutually perpendicular and similarly configured.

In one aspect, the frame coil is an angularly distributed coil which is arranged such that all loops thereof have a common intersection point, wherein a maximum angular distribution of the loops is no greater than approximately 40 degrees.

In one aspect, the second frame portion extends apically substantially throughout the entire length of the second housing member element.

In one aspect, the first coil portion surrounds the current modulator.

In one aspect, the coil is a ring coil.

In one aspect, a first ring coil portion is disposed within a first housing member element, a second ring coil portion is disposed within a second housing member element, and one or two segments extend between said first and second ring coil portions. The one or two segments that extend between said first and second ring coil portions may be a frame coil portion.

In one aspect, the coil is a frame coil which has an apical ring coil portion.

In one aspect, a wire extending from the coil portion mounted within the housing member is wound about an exterior surface of the housing member.

In one aspect, a wire extending from the coil portion mounted within the housing member is wound about an exterior surface of the root.

In one aspect, the implant device comprises a ferrite core insertable within the second housing member element.

In one aspect, the implant device further comprises a ferrite core insertable within the first housing member element.

In one aspect, the first and second coil portions are connected to the current modulator in parallel.

In one aspect, the current modulator comprises an oscillator, timer circuitry, an internal power source, and a switch for terminating electrical connection between said power source and said timing circuitry.

In one aspect, the current modulator further comprises an inverter for changing the radial direction of the generated electromagnetic field.

In one aspect, the timing circuitry is adapted to modulate a pulsed waveform in continuous ongoing fashion according to a desired duty cycle.

In one aspect, the timing circuitry is adapted to modulate a pulsed waveform for a predetermined modulation duration.

In one aspect, the generated electromagnetic field has a flux density ranging from 0.2 to 0.5 mT, 0.5 to 0.8 mT, 0.8 to 2 mT, 2 to 5 mT, or 0.2 to 5 mT.

In one aspect, the frequency of the pulsed current ranges from 1 Hz to 1000 Hz, 1 to 100 kHz, or 1 Hz to 100 kHz.

In one aspect, the pulsed current has an average amplitude ranging from 1 to 15 µA, 15 to 100 µA, 0.1 to 2 mA, or 1 to 2000 µA.

In one aspect, the pulsed current has a pulse duration ranging from 5 to 30 microseconds, 30 to 50 microseconds, 50 to 200 microseconds, or 5 to 200 microseconds.

In one aspect, the timing circuitry is adapted to modulate a pulsed waveform selected from the group consisting of a square waveform, a triangular waveform, a sawtooth shaped waveform, and a sinusoidal waveform.

In one aspect, the coil has a number of windings ranging from one to ten.

In one aspect, the power source is a battery that has a sufficient capacity for powering the current modulator during an entire anticipated healing period.

In one aspect, the power source is selected from the group consisting of a piezoelectric device for generating piezoelectricity in response to applied masticatory forces, a capacitor, a dynamo, and an electro-kinetic actuator.

The implant device is suitable in the field of implant dentistry, periodontal regeneration, orthodontic teeth movements, orthopedics, and neurology.

The implant device regulates proteoglycan and collagen synthesis and increase bone formation in models of endochondral ossification, accelerates bone formation and repair, increases union rates in fractures previously refractory to healing, and produce results equivalent to bone grafts.

In implant dentistry, the generation of electric and electromagnetic fields shortens the osseointegration time of the implant and improves the quality of the bone to implant contact.

The technological advantages of generating electromagnetic fields by the dental implant devices of the present invention include: (1) faster osseointegration—reduced healing time before teeth restoration; (2) better osseointegration—improved quality of bone to implant contact and therefore an increased implant success rate in poor bone quality conditions such as caused by osteoporosis and other bone systemic diseases, diabetes, elder patients, smokers and other environmental factors; (3) better bone formation (osteogenesis), for example in bone graft procedures; (4) fewer implant failures, and (5) a reduction in the number of surgical interventions.

In bone augmentation sites formed during ridge augmentation and sinus elevation procedures, the generation of electric and electromagnetic fields accelerates bone formation, shortens the time for bone remodeling and formation, and improves bone quality. As a result, the duration of the implant related treatment will be shortened and there will be fewer implants failures. Novel procedures such as placing implants together by a bone augmentation procedure will be made possible, reducing the number of surgical innervations.

In regenerative periodontal treatment, the generation of electric and electromagnetic fields induces an improved osteogenesis effect in restoring supporting bone in periodontal disease, enhancing the effect on the regeneration of periodontal tissues.

In orthodontic teeth movement, the generation of electric and electromagnetic fields during tooth movement increases the effect of the applied mechanical forces, leading to an enhancement of cell activation and tissue remodeling. Such an electrically stimulated cell-activating system will be as good as or even better than the currently used stress-related mechanism. The generation of electric and electromagnetic fields during tooth movement will decrease the orthodontic treatment time, decrease the relapse after treatment, and increase the range that teeth can be moved.

In orthopedics, the generation of electric and electromagnetic fields increases the healing of bone, cartilage and soft tissue after an orthopedic treatment.

In neurology, the generation of electric and electromagnetic fields in an area of neural damage will induce neural regeneration, for example as a result of an increased blood flow.

DETAILED DESCRIPTION OF PREFERRED EMBODIMENTS

The present invention is a novel implant device provided with an internal, constantly operable current modulator. The current modulator generates a radially directed electromagnetic field that propagates outwardly from the implant root to the implantation site and effectively stimulates osteogenesis. Osseointegration is also stimulated, so that when a dental implant device for example is employed, the required healing time prior to which a toothed crown cannot be engaged with the implanted root is dramatically reducing from 3-6 months to 4-12 weeks. Although the current modulator may be in constant operation, it is powered by a battery that does not need to be replaced or recharged by optimizing the modulation characteristics.

Figure 1:
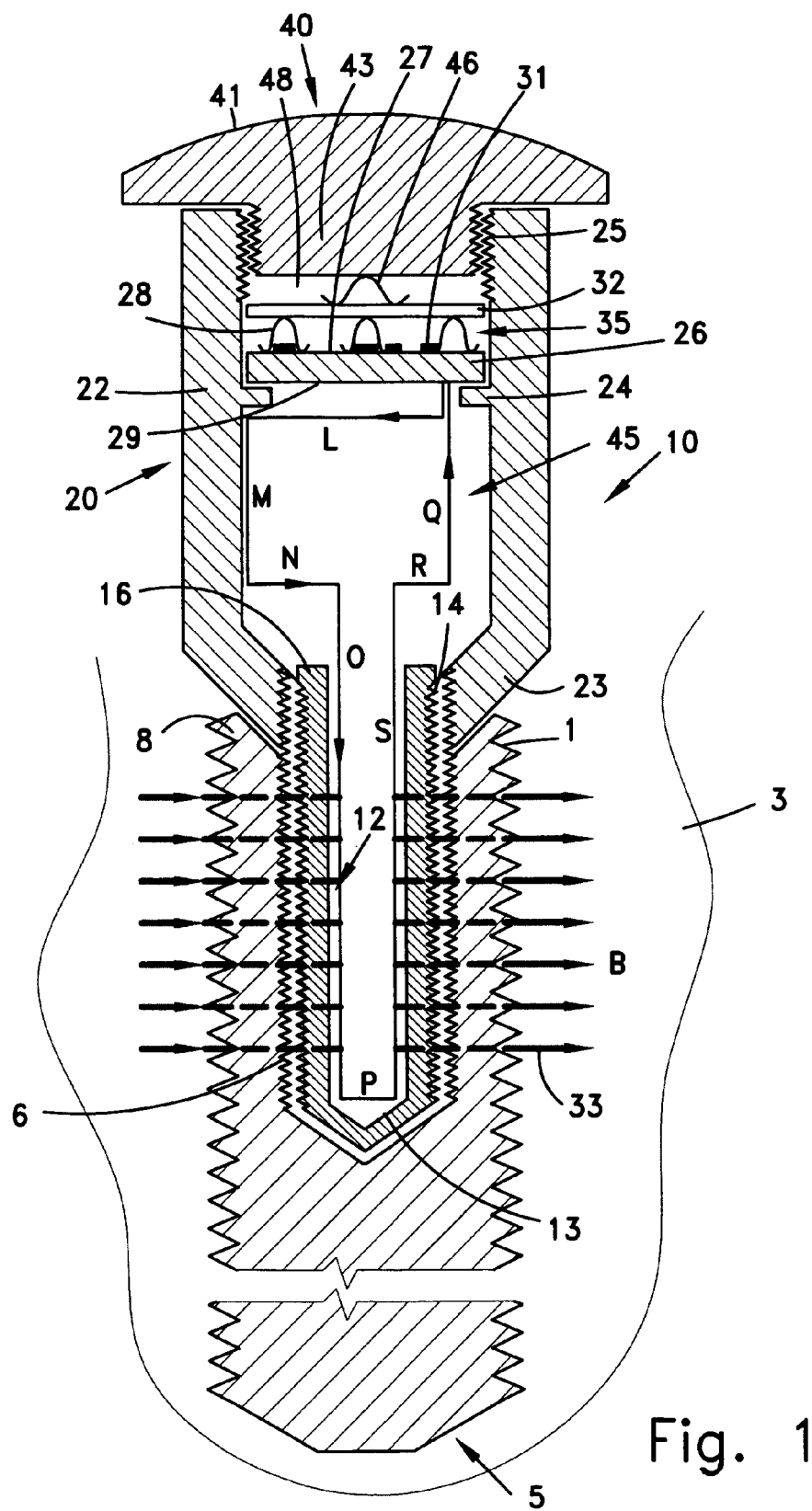
FIG. 1 is a schematic, cervical cross sectional view of an implant device according to one embodiment of the present invention, showing circular electromagnetic field lines that radiate outwardly from an internally mounted coil.

FIG. 1 schematically illustrates an implant device according to one embodiment of the present invention, generally indicated by numeral 10. Although the following description related to a dental implant device, it will be appreciated that the implant device is also suitable for stimulating osteogenesis and osseointegration in the fields of periodontal regeneration, orthodontic teeth movement, orthopedics, and neurology in addition to implant dentistry.

Implant device 10 comprises elongated, cervically extending implantable root 5 which is formed with outer threads 1 for effecting good penetration into the jawbone 3 as well known to those skilled in the art and with inner threads 6, an elongated hollow screw 12 formed with outer threads 14 for threadedly engaging the inner threads 6 of the implanted root 5, a hollow cap 20 having a U-shaped cross section for housing the circuitry of the current modulator, which may have the same configuration and dimensions of a prior art cap, and cover 40. As hollow screw 12 and cap 20 are used only during the tissue healing period, and are then replaced by a toothed crown, the interengaged abutment and cap may be referred to a "healing abutment".

Cap 20 is threadedly engageable with the coronal end 16 of hollow screw 12 that coronally protrudes from the coronal end 8 of root 5 and which is replaceable together with hollow screw 12 by the toothed crown upon completion of the healing time. Cover 40 has a coronal portion 41 which is wider than cap 20 and sealingly engageable therewith, and a central portion 43 narrower than coronal portion 41 which is threadedly engageable with threads 25 formed along the inner face of the coronal end of cap 20.

Cap 20 has coronally disposed and cervically extending straight walls 22, and curved walls 23 inwardly sloping from the apical end of wall 22 to allow engagement with abutment 12. One or more support elements 24 inwardly extend from straight walls 22, at an intermediate height thereof for supporting a printed circuit board (PCB) 26. Attached to the coronal side 27 of PCB 26 are a plurality of electronic components 31 and a plurality of electrically conducting leaf springs 28. A disc shaped battery 32 is placed in abutting relation with leaf springs 28. The battery 32 may be a Nickel-Cadmium (NiCd) battery, with a capacity of 6.4 mA/hour, so as to provide current pulses in the range of e.g. 5-15 µA for a time period of approximately 6 weeks. An electrically isolating leaf spring 48 is attached to the apical surface 48 of cover 40, so that when cover 40 is engaged with cap 20 to a fullest extent, battery 32 is pushed in electrical contact with PCB 26 by means of leaf springs 28 and 46 to initiate operation of current modulator 35.

It will be appreciated that battery 32 may be placed in electrical connection with PCB 26 by many other methods well known to those skilled in the art.

Current modulator 35 may be powered by any other power source well known to those skilled in the art, including a piezoelectric device for generating piezoelectricity in response to applied masticatory forces, such as those applied during conversation or during a meal, a capacitor which is charged by a radiofrequency device located at the home of an implantee and therefore would not require outpatient services, a dynamo, and an electro-kinetic actuator, for example one which employs a magnetic element that is displaceable along a coil.

Connected to the apical side 29 of PCB 26 is continuous frame coil 45, only one loop of which is shown for clarity. Coil 45 has a coronal radial portion L extending substantially the width of wall 22, a cervical portion M extending apically from portion L, an inwardly extending radial portion N extending from portion M, and a cervical portion O extending apically from portion N to substantially a terminal surface 13 of abutment 12. Portions Q-S of coil 45 are symmetrical to portions M-O, respectively. A portion P extends radially between portions O and S.

Upon operation of current modulator 35, an electromagnetic field B radially directed outwardly from coil 45 is generated. Electromagnetic field B may be visualized by a plurality of concentric circular field lines 33 that radiate outwardly from coil 45. The applicants have surprisingly discovered that electromagnetic field B is effective in stimulating osteogenesis and osseointegration of root 5, which is preferably made of titanium or of a titanium alloy by virtue of its good biocompatibility and electromagnetic transmitting properties, with respect to the surrounding jawbone 3 while current modulator 35 is able to operate in an ongoing fashion throughout a predetermined shortened treatment duration of 4-12 weeks.

The applicants have found that a magnetic flux density generated by current modulator 35 which may range from 0.2 to 0.5 mT is effective in terms of stimulating osteogenesis and osseointegration in the vicinity of root 5, the value of 0.2 mT being the threshold of efficacious osteogenesis stimulation for a frequency of 100 Hz and a pulse width of 25 µs [Matsumoto, H et al, "Pulsed Electromagnetic Fields Promote Bone Formation around Dental Implants Inserted into the Femur of Rabbits", Clin Oral Impl Res 2000: 11: 354-360].

As described in Example 5, the attenuation of the generated electromagnetic field while being transmitted through an implant device made of a titanium alloy at a currency frequency of 1 kHz is negligible. The aforementioned range of magnetic flux density will therefore be effective in stimulating osteogenesis at an electromagnetic field propagation distance extending radially from root 5 of approximately 2 mm, corresponding to the thickness of the damaged tissue layer.

The following combination of parameters has been found to be effective in achieving osteogenesis and osseointegration stimulation for a pulsed current modulator housed within the implant device of the present invention:
  a) a frequency range of 1 Hz to 100 kHz, and preferably of 10 Hz for allowing efficient metal penetration;
  b) a magnetic flux density range of 0.2 to 0.5 mT, 0.5 to 0.8 mT, 0.8 to 2 mT, or 2-5 mT;
  c) an electromagnetic field propagation distance L extending radially from root 5 of up to 5 mm, and preferably of 2 mm, corresponding to the thickness of the damaged tissue layer resulting from implantation and to the selected magnetic flux density range;
  d) a pulse duration of 5-30, 30-50, or 50-200 microseconds;
  e) an average current magnitude of 1-15 µA, 15-100 µA, or 0.1-2 mA;
  f) a square, triangular, sawtooth, or sinusoidal waveform; and
  g) a predetermined number of coil windings ranging from 1-10.

Figure 12:
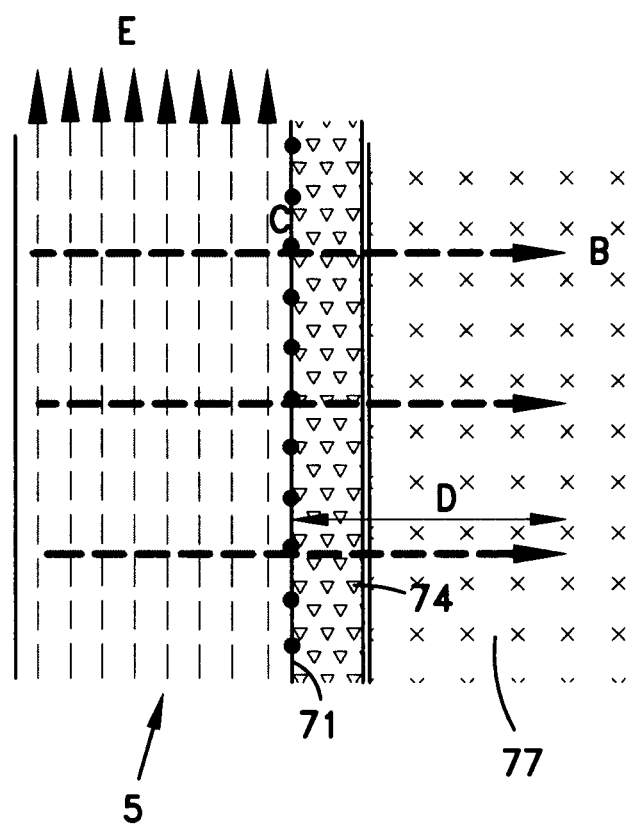
FIG. 12 schematically illustrates the osseointegration of a narrow bone region to the outer surface of the implant device by means of an electric field E induced by the propagation therethrough of the generated magnetic field.

Another advantage of the implant device of the present invention is that the generated magnetic field B will cause root 5 to be charged when made of an electrically conductive material such as titanium. As schematically illustrated in FIG. 12, an electric field E generated by eddy currents is induced when the electrically conductive wall of root 5 encounters the varying magnetic field B. The induced eddy currents are in an opposite radial direction to the radial direction of the circular field lines of electromagnetic field B, and the repulsive force between the eddy currents and the magnetic field lines generated electric field E. Outer wall 71 of root 5, which is schematically shown as a straight wall but in reality will generally assume another shape due to the presence of the threading, carries a charge C by means of electric field E. As the charged outer wall 71 of root 5 interfaces with the adjacent bone region, a narrow bone region 74 having a thickness of approximately 10 microns becomes osseointegrated with outer wall 71. Electromagnetic field B propagates outwardly from narrow bone region 74 for a propagation distance D to a thicker bone region 77, thereby stimulating osteogenesis within thicker bone region 77 disposed outwardly from osseointegrated bone region 74.

Figure 7:
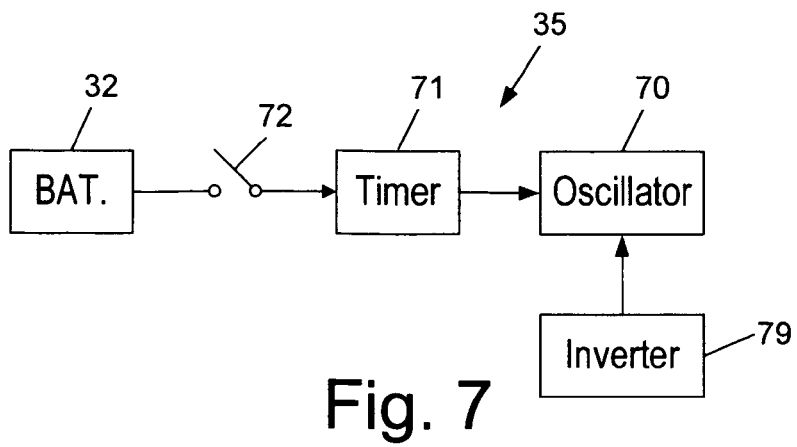
FIG. 7 is a block diagram of the current modulator.

FIG. 7 is a block diagram of current modulator 35. Current modulator 35 comprises an oscillator 70, timer circuitry 71, an on/off switch 72 and a battery 32, or any other suitable power source as described hereinabove. Oscillator 70 is adapted to generate a plurality of current pulses, e.g. rectangular pulses, for exciting the coil by a desired frequency and magnitude, so as to induce a desired magnetic flux. Of course, other waveforms, such as a triangular, sawtooth, and sinusoidal waveform, may also be used to excite the coil. Timer circuitry 71 modulates the waveform by periodically deactivating power supply 32 to oscillator 70 by means of switch 72, in order to achieve a desired duty cycle which is essential for saving energy. Switch 72 may be a mechanical DC switch which is normally set at its off, or non-conducting, state. In order to save battery power, switch 72 may be automatically activated to its conducting state only upon screwing and tightening cover 40 with respect to cap 20, as schematically illustrated in FIG. 1.

If so desired, current modulator 35 may also comprise an inverter 79 in electrical communication with oscillator 70, for periodically changing the radial direction of the magnetic field lines and for thereby additionally improving the rate of osteogenesis and osseointegration.

Figure 8:
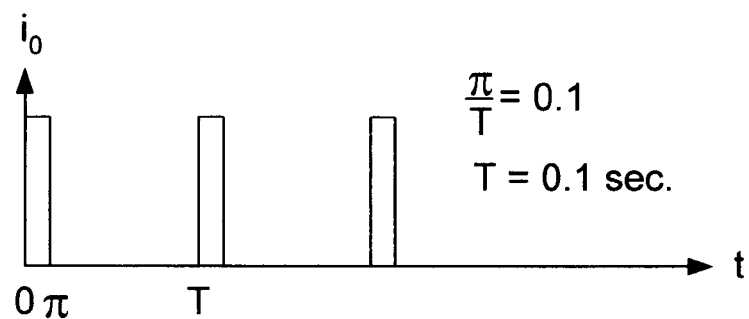
FIG. 8 schematically illustrates an exemplary current waveform for exciting the magnetic flux in the coil.

FIG. 8 schematically illustrates an exemplary current waveform that is used to excite the magnetic flux in the coil. In this example, the current amplitude is 8.4 µA, the frequency is 10 Hz and the duty cycle is 10%. These parameters induce a magnetic flux of 0.2-0.5 mT in the close vicinity of the implant device. The timing circuitry is adapted to generate this waveform in continuous ongoing fashion according to the desired duty cycle.

Alternatively, the timing circuitry may be adapted to modulate the waveform for a predetermined modulation duration, e.g. four hours. The switch is set to a constant non-conducting state after the predetermined modulation duration elapses until commencement of another modulation duration. The duration of each pulse that is generated during the modulation duration may be selected so as to be longer than the pulse duration of the continuous ongoing waveform of a 10% duty cycle, ensuring that the total accumulated amount of energy will be absorbed during a predetermined period by the bone region spaced from the root at a distance less than the predetermined electromagnetic field propagation distance.

Figure 9:
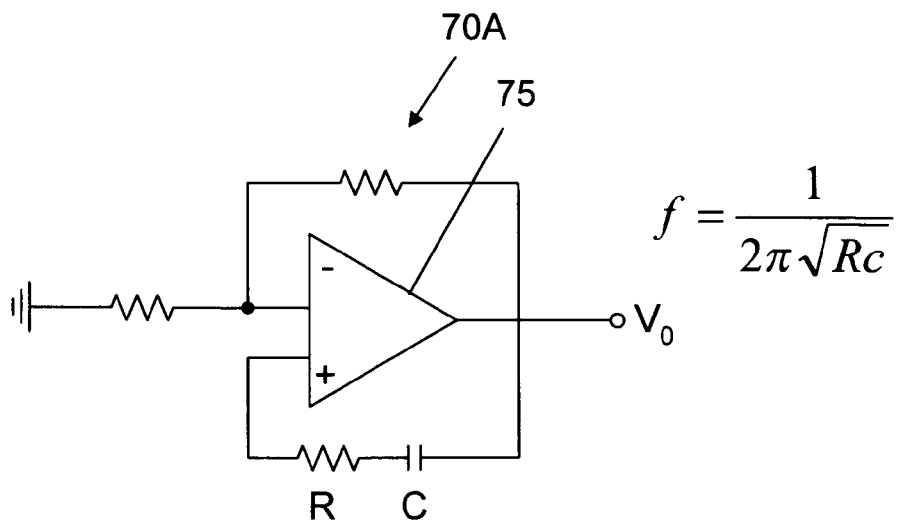
FIGS. 9 and 10 schematically illustrate two configurations, respectively, of the oscillator of FIG. 7.
Figure 10:
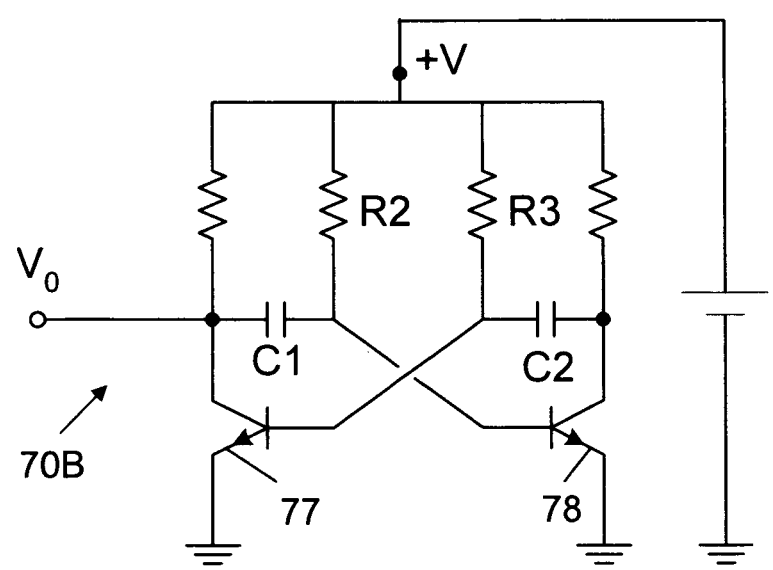

FIGS. 9 and 10 illustrate two exemplary configurations of the oscillator. In FIG. 9, oscillator 70A is implemented using an operational amplifier 75 with a regenerative feedback resulting from a series connection of a resistor R and a capacitor C from output to input. The frequency is determined by the values of R and C.

Another possible implementation of the oscillator is by using a stable multivibrator, as shown in FIG. 10. In this configuration of an oscillator 70B, both transistors 77 and 78 are coupled to each other through capacitors C1 and C2. A transistor that is off at any moment cannot remain off indefinitely since its base will become forward biased when a capacitor is being charged towards +V. Once a capacitor is completely charged, a first transistor will turn on, thereby turning the second transistor off. This way, the circuit is not stable in either state—it continuously oscillates from one state to the other. Again, frequency is determined by the values of resistors and capacitors.

Many different coil configurations may be employed in order to increase the magnetic flux density or to cause the magnetic flux density to be distributed in a distributed in a desired fashion.

Figure 2A:
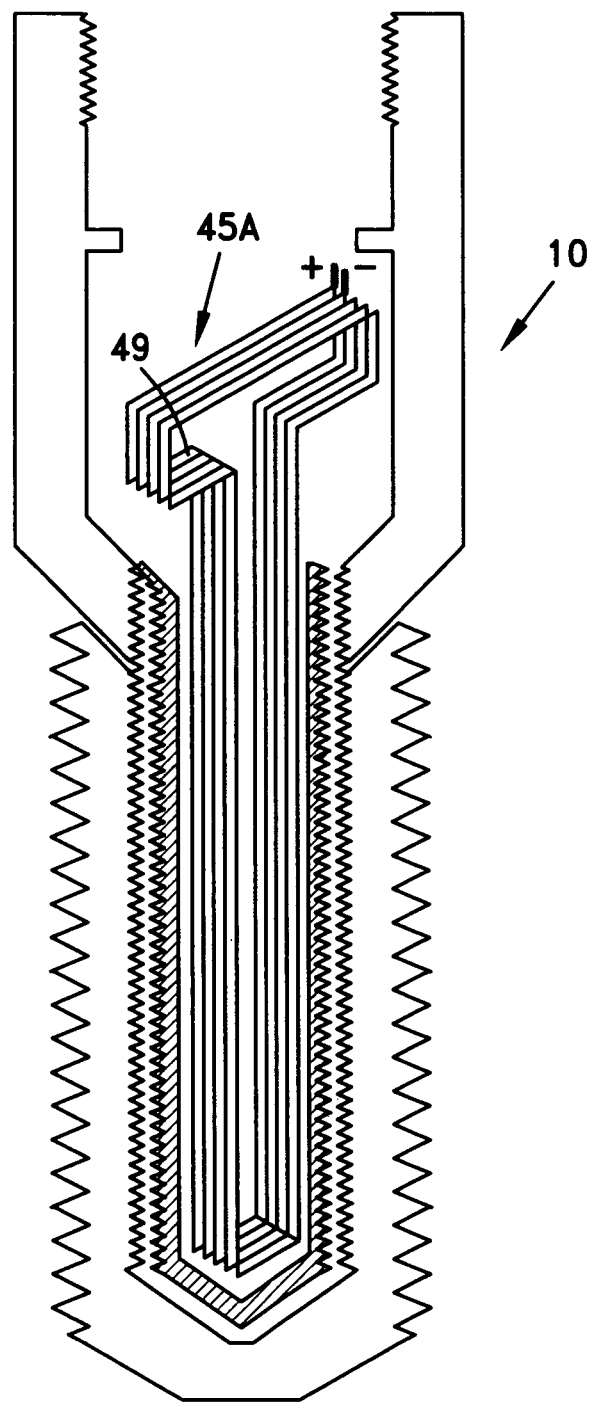
FIG. 2A is a schematic perspective view of a continuous frame coil arranged with a plurality of aligned loops which is mounted within the implant device of FIG. 1.

FIG. 2A illustrates implant device 10 provided with continuous frame coil 45A arranged with a plurality of aligned loops 49.

Figure 2B:
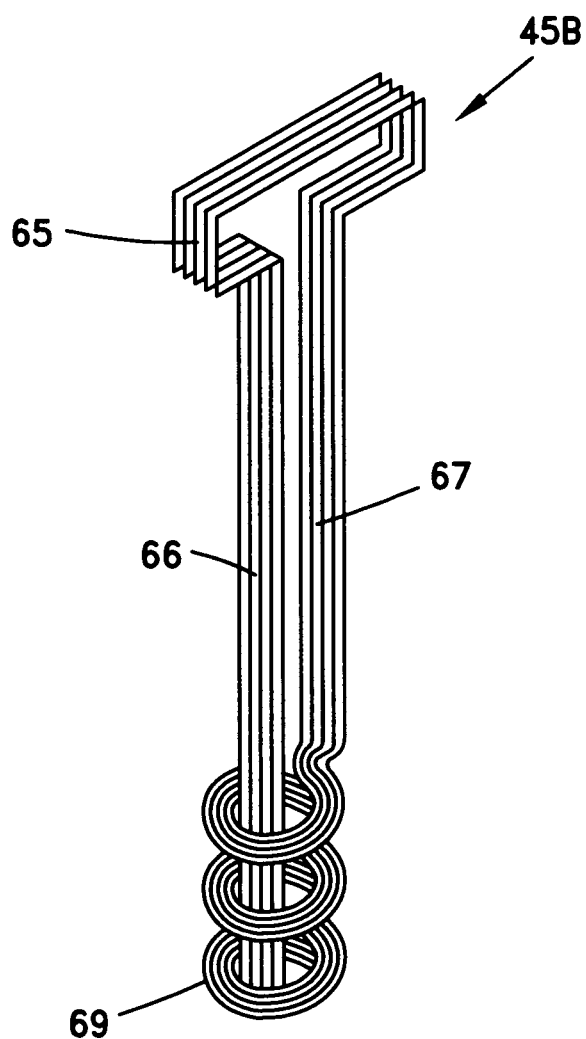
FIG. 2B is a schematic perspective view of a continuous coil provided with a coronal frame coil portion and an apical ring coil portion.

FIG. 2B illustrates a continuous coil 45B which comprises a coronal frame coil portion 65 and an apical ring coil portion 69. Parallel segments 66 and 67 cervically extend from portions 65 to 69.

Figure 3:
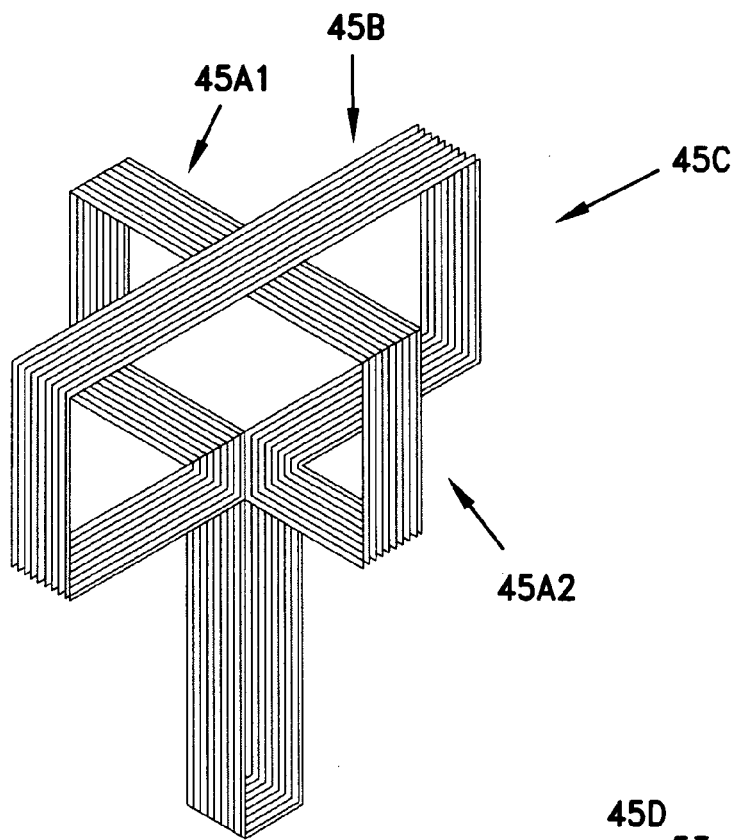
FIG. 3 is a schematic perspective view of a continuous coil comprising two mutually perpendicular frame coil sections, each of which having a similar but differently oriented arrangement.

FIG. 3 illustrates a continuous coil 45C comprising two mutually perpendicular frame coil sections 45A1 and 45A2, each of which having a similar but differently oriented arrangement.

Figure 4:
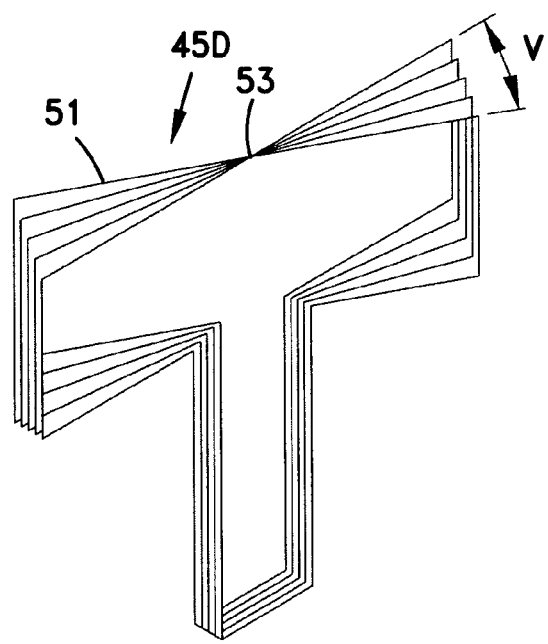
FIG. 4 is a schematic perspective view of an angularly distributed coil wherein all of the loops have a common intersection point.

FIG. 4 illustrates an angularly distributed coil 45D wherein all of the loops 51 have a common intersection point 53. The maximum angular distribution V of the loops should preferably be no greater than approximately 40 degrees to prevent electromagnetic field cancellation effects.

Figure 5:
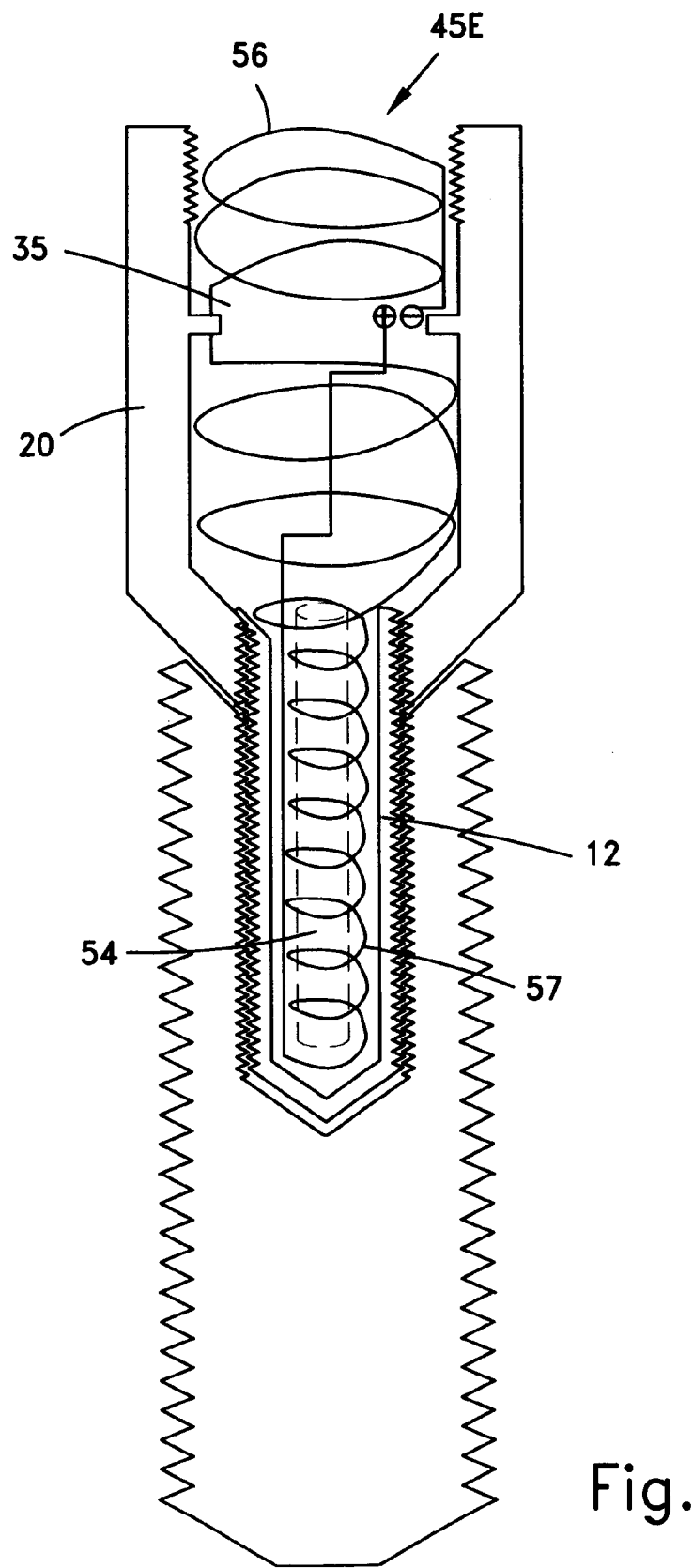
FIG. 5 is a schematic, cervical cross sectional view of a ring coil mounted within the implant device of FIG. 1 and having a first large-diameter portion and a second small-diameter portion.

FIG. 5 illustrates a continuous ring coil 45E which comprises a first large-diameter portion mounted within cap 20 and a second small-diameter portion 57 mounted within hollow screw 12. First portion 56 may be sized to encircle current modulator 35 while second portion 57 may be sized to apically extend throughout the interior of hollow screw 12. A ferrite core 54, e.g. a rod, for increasing the magnetic permeability may be inserted internally within second portion 57.

A coil may also comprise a first ring coil portion mounted within cap 20, a second ring coil portion mounted within hollow screw 12, and two straight segments connecting the two ring coil portions. Alternatively, a frame coil portion may be interposed between the two ring coil portions.

Other combinations of other coil portions described herein are also within the scope of the invention.

Figure 15:
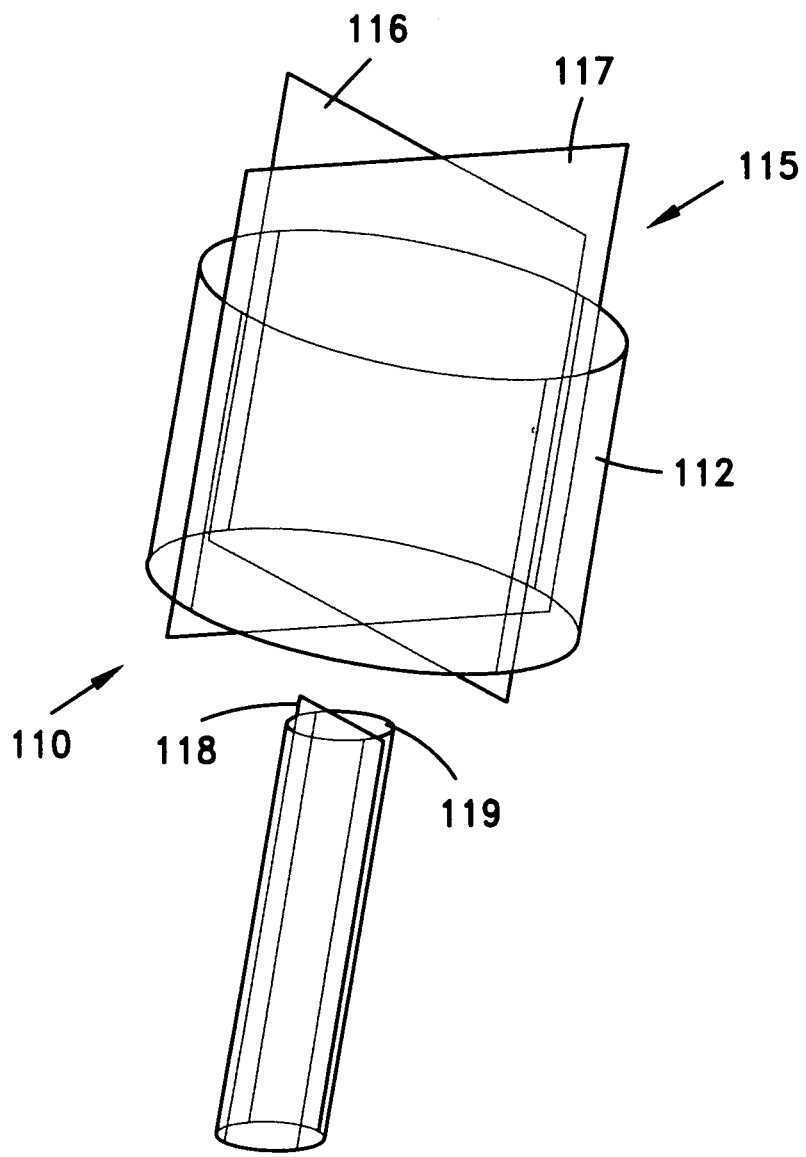
FIG. 15 is a schematic illustration of a coil assembly, according to another embodiment of the present invention.

FIG. 15 schematically illustrates a coil assembly 110, according to an embodiment which may be a best mode of the invention. Coil assembly 110 comprises a first coil portion 115 provided with two mutually perpendicular frame coil sections 116 and 117, which are configured similarly to sections 45A1 and 45A2, respectively, shown in FIG. 3 and which are mountable within the implant device cap, and a second frame coil portion 118 mountable within the hollow screw. Coil portions 115 and 118 are connected to the current modulator in parallel. Both coil portions 115 and 118 may be made of only one winding, in order to reduce inductance and resistance.

If so desired, a ring coil comprising one or more loops may be provided at the apical end of frame coil portion 118 in the fashion shown in FIG. 2B, or alternatively, may be positioned separately from frame coil portion 118.

A ferrite core may be positionable within the interior of each of the first coil portion 115 and the second coil portion 118 such that the coil is wound about the corresponding ferrite core. The ferrite core 112 associated with first coil portion 115 may be cylindrical and the ferrite core 119 associated with second coil portion 118 may be elliptical to account for the thickness of the leads wire, or may be configured in any other fashion.

Figure 6A:
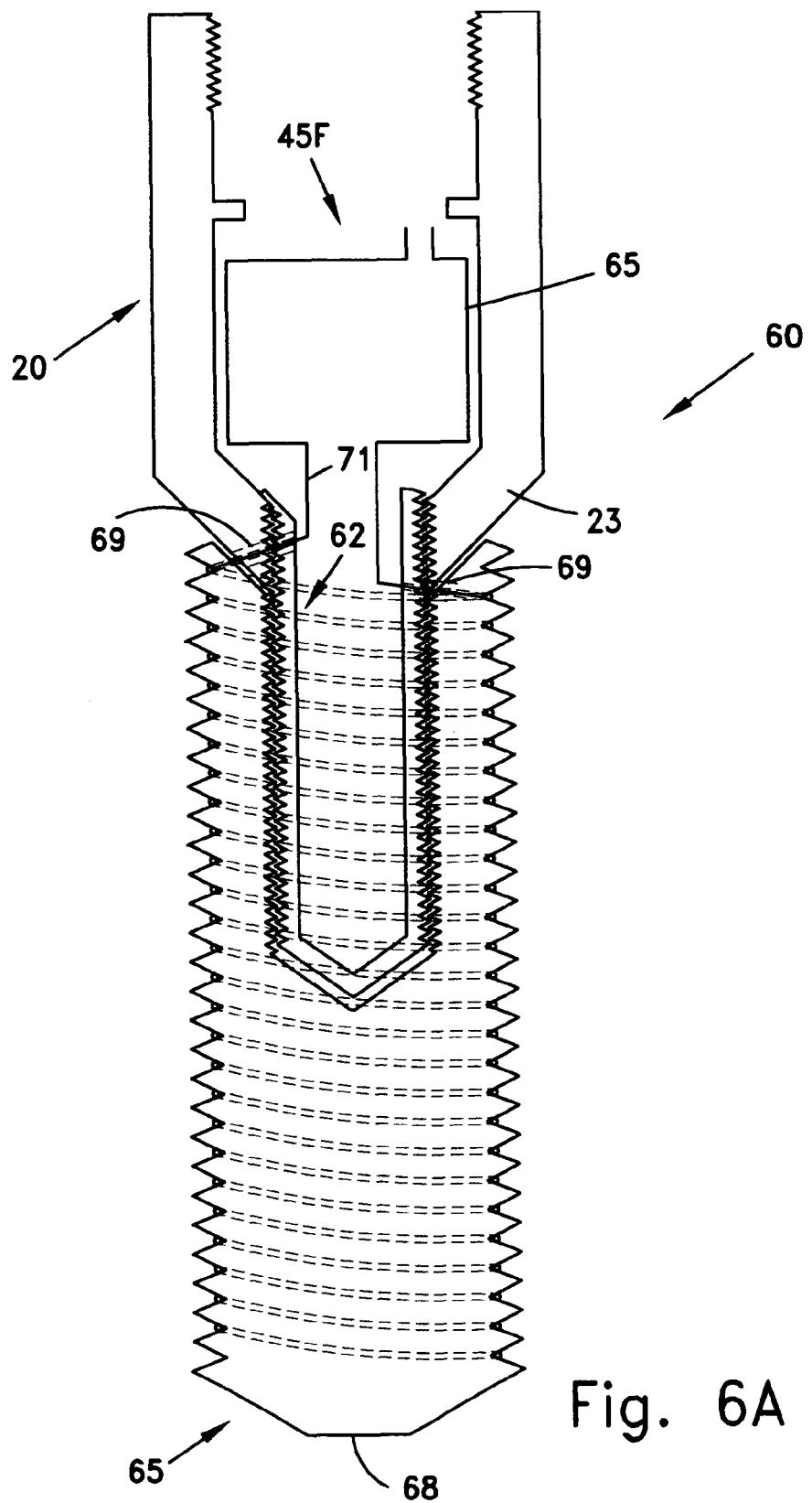
FIG. 6A is a schematic, cervical cross sectional view of an implant device according to another embodiment of the present invention, showing a coil having a frame coil portion mounted within the cap of the implant device and a wire which winds about the exterior surface of the root.

FIG. 6A illustrates an implant device 60 having a coil 45F with a first frame coil portion 65 and with a second wire portion 71 extending from frame coil portion 65 and winding about the exterior surface of root 65 and along a predetermined depth thereof, which may correspond to the entire length of root 65 to substantially its apical end 68 as shown to maximize osteogenesis and osseointegration stimulation, or to any other desired depth. Cap 20 is configured similarly to that of device 10 illustrated in FIG. 1. At least two, and possibly three, of the components selected from cap 20, hollow screw 62, and root 65 are formed with a plurality of openings. Each set of openings, e.g. a first formed in hollow screw 62 and a second formed in cap 20, defines an aligned passageway, e.g. passageway 69, through which the wire 71 is introduced so that it may be wound about the exterior surface of root 65.

Figure 6B:
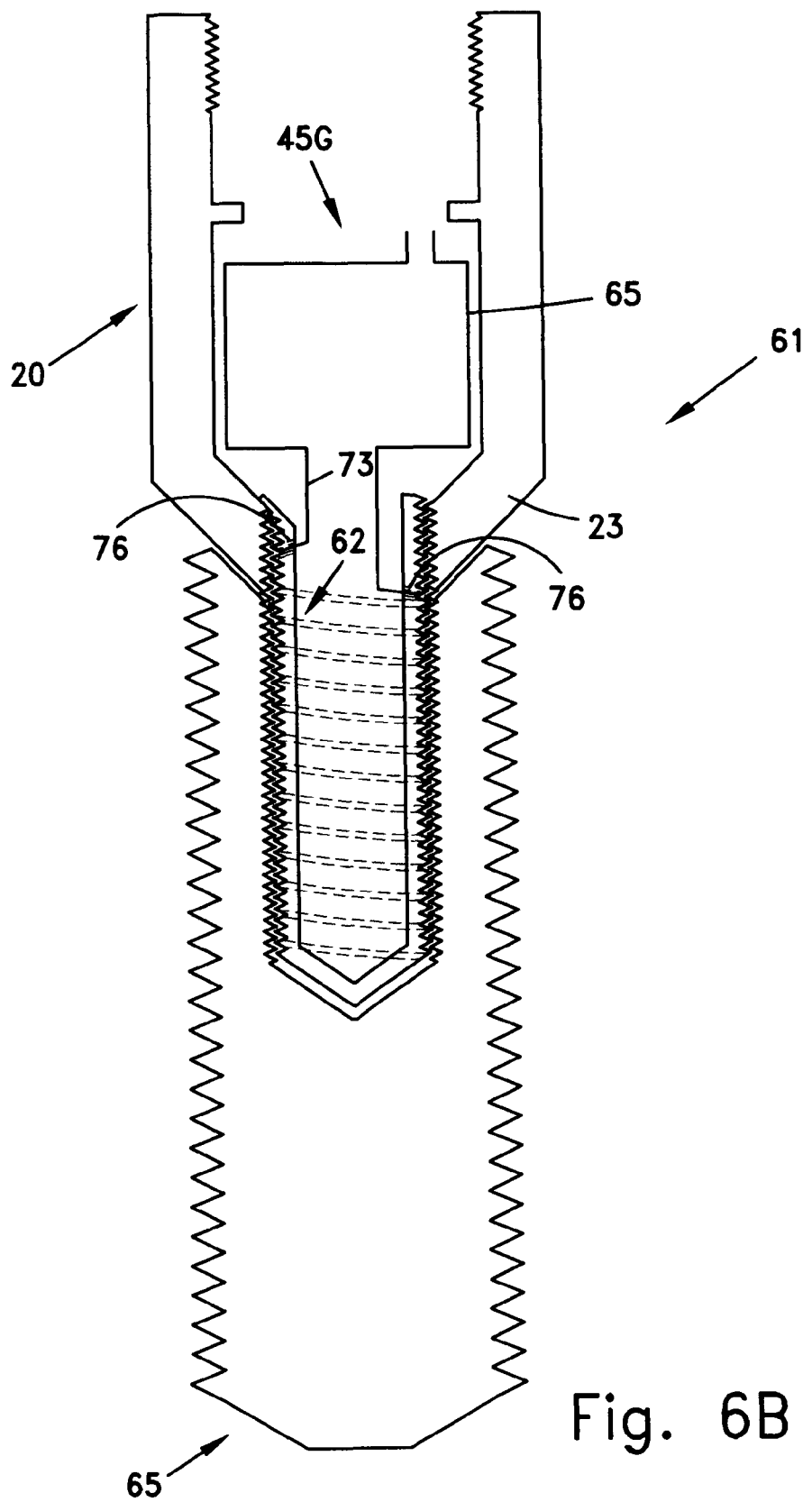
FIG. 6B is a schematic, cervical cross sectional view of an implant device according to another embodiment of the present invention, showing a coil having a frame coil portion mounted within the cap of the implant device and a wire which winds about the exterior surface of the hollow screw.

FIG. 6B illustrates an implant device 61 having a coil 45G with a first frame coil portion 65 and with a second wire portion 73 which winds about the exterior surface of hollow screw 62. Hollow screw 62 is formed with passageways 76 through which the wire 73 is introduced so that it may be wound about the exterior surface of hollow screw 62.

Figure 6C:
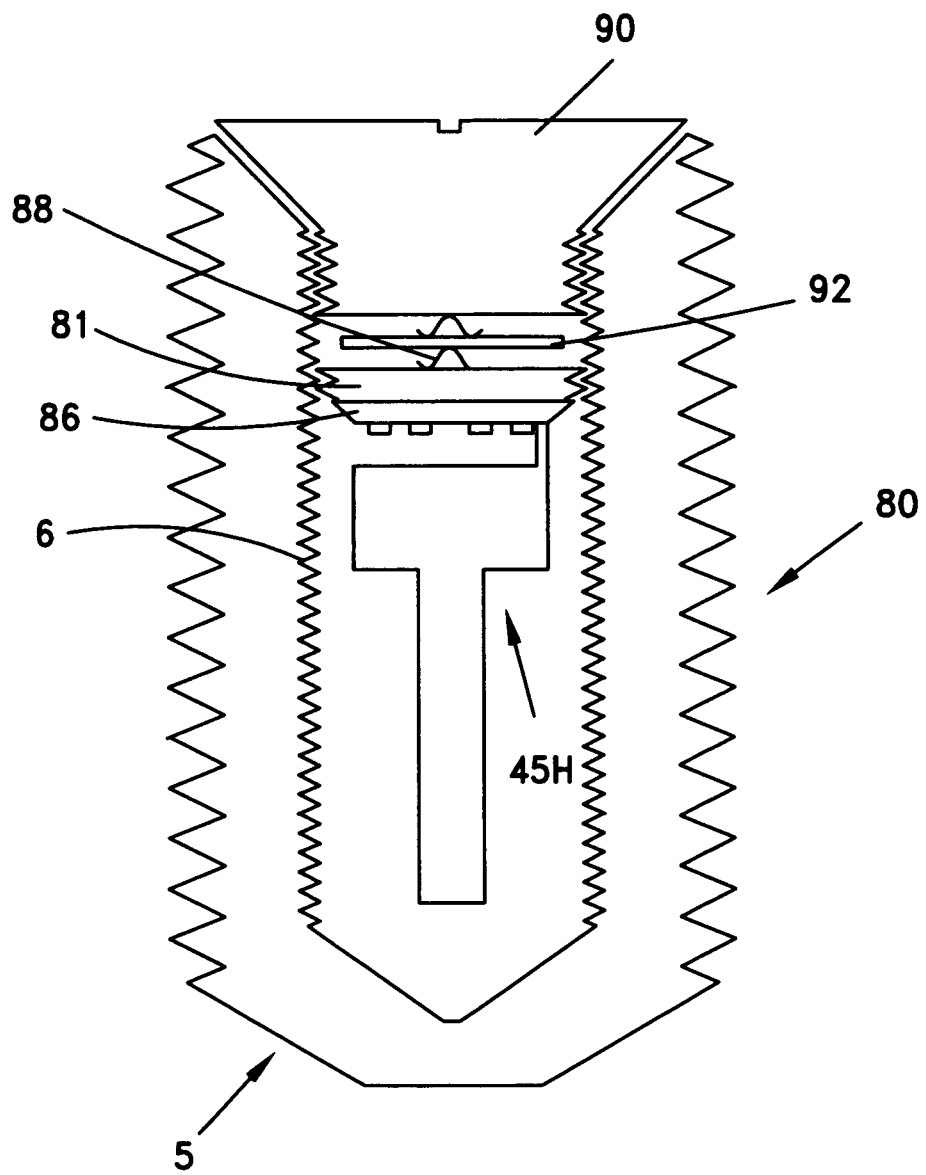
FIG. 6C is a schematic, cervical cross sectional view of an implant device without a cap, showing a frame coil which is mounted therewithin.

FIG. 6C schematically illustrates a dental implant device 80 that is configured without a cap, according to another embodiment of the present invention. In this embodiment, all the electric components are confined within the interior of the implantable root 5, without the need for an abutment or a hollow cap for housing the circuitry of the current modulator. A sealing screw 90 is used to cover the opening of root 5, and is adapted to slightly protrude from the gingiva. The sealing screw 90 is used only during the tissue healing period, and is then replaced by a toothed crown.

A circular support element 81 may be threadedly engaged with the threads 6 formed along the inner face of the implant root 5. PCB 86 carrying the electronic components is attached, e.g. by bonding, to the apical side of support element 81. A power source 92 coronally separated from PCB 86 is placed in electrical connection therewith by means of leaf springs 88 upon engagement of sealing screw 90 with root 5, or by any other means well known to those skilled in the art. Connected to the apical side 28 of PCB 86 is continuous frame coil 45H, only one loop of which is shown for clarity, as illustrated and described with respect to FIG. 1, or configured in any other desired fashion.

Example 1

Magnetic Flux Density Distribution

Figure 11:
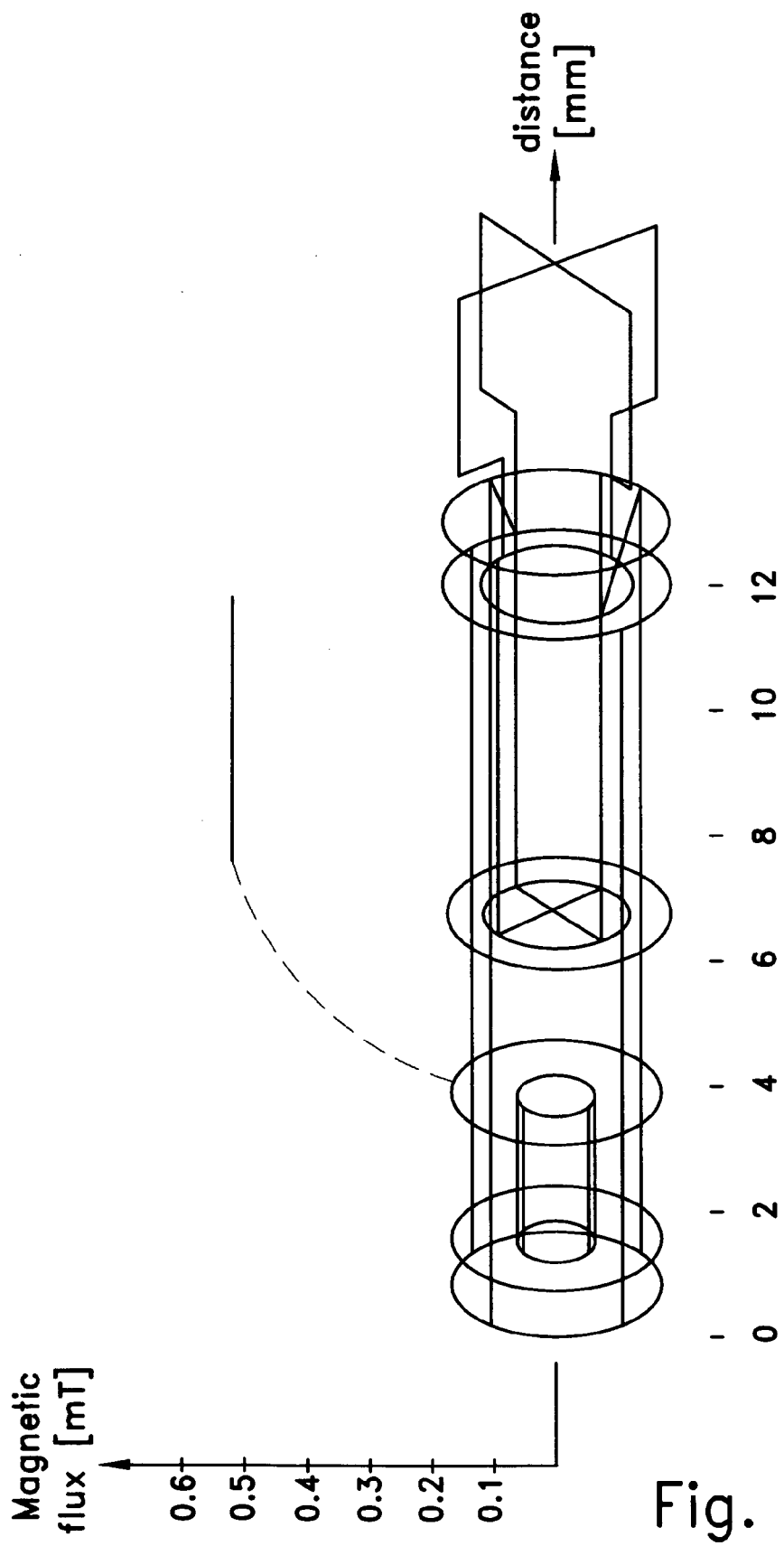
FIG. 11 is a simulation of the magnetic flux generated by means of two mutually perpendicular frame coils that are mounted within an implant.

FIG. 11 is a simulation of the magnetic flux that is generated by means of two mutually perpendicular frame coils similar to those illustrated in FIG. 3 although with only winding and of an extension coil mounted within an implant. The coil is disposed within the open void of the implant, up to a height of 7 mm from the apical end of the implant device. The magnetic flux density distribution is shown as a function of the cervical distance from the apical end of the implant device, as indicated in Table I.

TABLE I

| | Height [mm] | | | | | |
|---|---|---|---|---|---|---|
| | 12 | 10 | 8 | 6 | 4 | 2 |
| Maximal magnetic flux density [mT] | 0.56 | 0.58 | 0.52 | 0.17 | 0.04 | 0.017 |

Example 2

Magnetic Flux Density Distribution with Ferrite Core

The magnetic flux density distribution for the coil assembly of FIG. 15 was simulated based on two mutually perpendicular frame coils, each of which having a height of 5 mm and a width of 5 mm and a wire diameter of 0.4 mm. The apical edge of the frame coil was selected to be separated 13 mm from the apical end of the implant device, and the coronal edge of the frame coil was selected to be separated 18 mm from the apical end of the implant device.

The cylindrical ferrite core associated with the cap was selected to have a diameter of 4.5 mm and a height of 3.1 mm. The apical edge of the cylindrical ferrite core was selected to be separated 13.3 mm from the apical end of the implant device, and its coronal edge was selected to be separated 16.4 mm from the apical end of the implant device. The elliptical ferrite core associated with the hollow screw was selected to have a major axis of 1.3 mm, a minor axis of 0.8 mm, and a height of 4.4 mm. The apical edge of the elliptical ferrite core apical edge was selected to be separated 7.5 mm from the apical end of the implant device, and its coronal edge was selected to be separated 11.9 mm from the apical end of the implant device. The relative permeability of both ferrite cores was selected to be at least 2000.

The electromagnetic field that was simulated was based on a current of 6 µA in the cap coil, a current of 3.6 µA in the hollow screw coil, and a frequency of 22.2 kHz. The generated magnetic flux density profile along an apically extending line at a distance of 1 mm outwardly from the implant indicated that between a separation of 12 and 6 mm from the apical end of the implant device, the flux density ranged between 0.5 and 0.12 mT. At a cervical separation of 8 mm from the apical end of the implant device, the flux density at a distance of up to 2 mm radially outwardly from the implant device was found to be greater than 1.2 mT.

Example 3

Skin Effect

Prior to determining the magnetic field attenuation of an exemplary tube provided with an internal magnetic field source, having a relatively large ratio of axial length to radial length, and made of titanium alloy, the attenuation at a portion thereof which is internal to the tube outer edge (hereinafter the "skin") is first evaluated.

The decrease in current density from the inner to outer surface of the tube is given by the following equation:

$$J(d) = J_s \exp(-d/\delta),\qquad\text{Equation (1)}$$

where J is the current density, $J_s$ is the current density at the inner surface, d is a given thickness within the tube from its inner surface, and δ is given by the following expression:

$$\delta = \sqrt{\frac{\rho}{\pi f \mu}}, \quad \text{Equation (2)}$$

where ρ is the tube resistivity, μ is the tube magnetic permeability, and f is the magnetic field frequency.

For the titanium alloy used for implants, ρ=1.75 10^(−6) Ωm and μ=1.00005*4π 10^(−7) N/A. Thus for a frequency of f=1 kHz, δ=21 mm, while for a frequency of f=1 MHz, δ=0.67 mm, where δ is the depth at which the current density is attenuated to 1/e or about 0.37 of its initial value.

For a tube thickness of 0.5 mm corresponding to the approximate thickness of an implant wall, the skin effect is negligible for a frequency of 1 kHz, while the current density at the outer tube surface at 1 MHz is reduced to about one-half of its value at the inner surface.

Example 4

Induced Current at Inner Surface

The electromotive force ε is equal to the time derivative of the magnetic flux Φ:

$$\varepsilon = \frac{\partial \Phi}{\partial t} = \frac{\partial}{\partial t} \int B \, da, \quad \text{Equation (3)}$$

or $$\varepsilon = 2\pi r \rho J_S, \quad \text{Equation (4)}$$

where ρ is the tube resistivity, B is the magnetic field magnitude, and $J_s$ is the current induced by the magnetic field.

A time harmonic and spatially constant magnetic field B of the following form is assumed for simplicity:

$$B = B_0 \cos(2\pi f t), \quad \text{Equation (5)}$$

where f is the frequency. The solution for Equation 3 therefore becomes:

$$\frac{\partial \Phi}{\partial t} = \pi r^2 * 2\pi f B \quad \text{Equation (6)}$$

The dependence of the current density at the inner tube surface on the magnetic field magnitude is therefore:

$$J_S = \frac{\pi f r B}{\rho} \quad \text{Equation (7)}$$

Example 5

Magnetic Field Attenuation

A magnetic field B is induced along the longitudinal axis of the tube, and current J therefore flows along the tube perimeter. The magnetic field integral is calculated along a surface S.

From Maxwell's equations it is derived that the integral of magnetic field B along the surface S equals the integral of the current J over the area A enclosed by the surface S:

$$\int_S B \, ds = \mu \int_A J \, da, \quad \text{Equation (8)}$$

where μ is the permeability of the tube material.

At a tube portion internal to the tube edges, the left side of Equation 8 is equal to hΔB, where h is the circumferential length of the surface S, and ΔB is the change in B from the inner to the outer surface of the tube.

Since the skin effect is negligible for a frequency of 1 kHz as described in Example 2, the current density $J_s$ along the tube layer from its inner to outer surface can be considered constant (J=$J_s$). Hence the right side of Equation 8 is equal to $\mu J_s h l_c$, where the tube thickness is $l_c$, resulting in the following equation:

$$\Delta B = \mu J_s l_c. \quad \text{Equation (9)}$$

Substituting the attenuation distance δ defined in Example 3 and the current density $J_s$ from Equation 7 described in Example 4 results in the expression:

$$\Delta B = \frac{\mu \pi f r l_c}{\rho} B = \frac{r l_c}{\delta^2} B, \quad \text{Equation (10)}$$

The relative attenuation At of the magnetic field across the tube thickness defined as ΔB/B is therefore equal to:

$$At = \frac{r l_c}{\delta^2} \quad \text{Equation (11)}$$

For a tube thickness $l_c$ of 0.5 mm, a tube radius r of 2.1 mm, an attenuation distance δ of 21 mm for a frequency f of 1 kHz, the attenuation across the tube thickness is a negligible value of only 0.24%.

Since the skin effect has to be considered for a frequency of 1 MHz, a circumferential tube portion is integrated and the right side of Equation 8 is therefore equal to:

$$\mu \int J \, da = \mu h \int_0^{l_c} J_S e^{-y/\delta} \, dy = \mu h J_S \delta (1 - e^{-l_c/\delta}), \quad \text{Equation (12)}$$

or $$\Delta B = \mu J_S \delta (1 - e^{-l_c/\delta}) \quad \text{Equation (13)}$$

After substituting the current density $J_s$ from Equation 7, the following relation follows:

$$\Delta B = \frac{r(1 - e^{-l_c/\delta})}{\delta} B, \quad \text{Equation (14)}$$

resulting in an attenuation At of:

$$At = \frac{r(1 - e^{-l_c/\delta})}{\delta} \quad \text{Equation (15)}$$

For a tube thickness $l_c$ of 0.5 mm, a tube radius r of 2.1 mm, an attenuation distance δ of 0.67 mm for a frequency f of 1 MHz, the attenuation across the tube thickness is 1.64, meaning that the radial direction of the generated magnetic field will be changed to an opposite radial direction.

Although being dependent upon the tube thickness $l_c$, the frequency f, the resistivity $\rho$ and the permeability $\mu$, it will be appreciated that the attenuation At may be dependent upon the tube radius r by a different relation than that which is set forth in Equation 15 for other magnetic field profiles.

Figure 13:
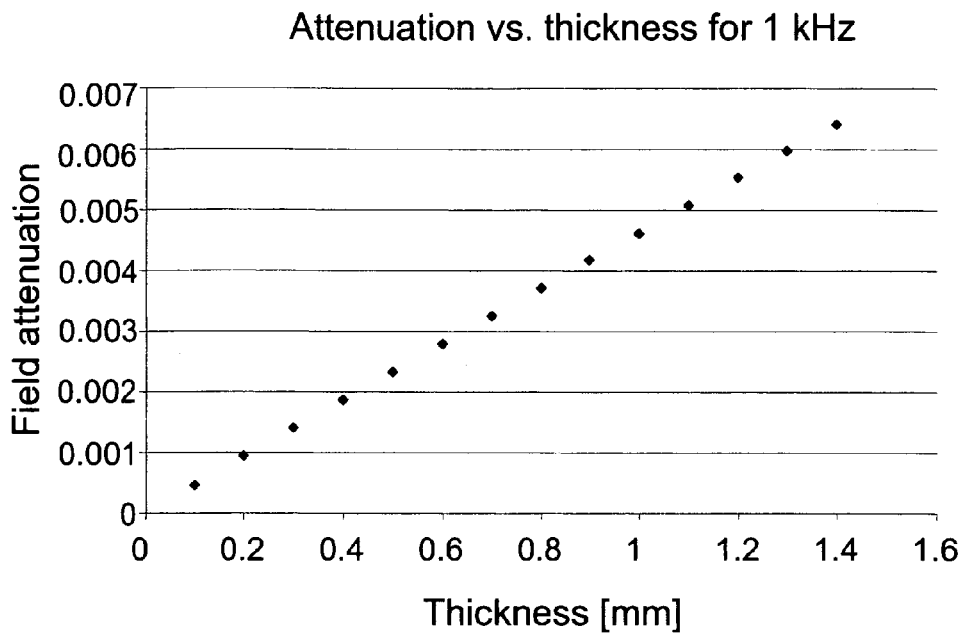
FIG. 13 is a graphic illustration of the magnetic field attenuation as a function of tube thickness.

FIG. 13 graphically illustrates the magnetic field attenuation as a function of tube thickness for a frequency of 1 kHz, based on Equation 15.

Figure 14:
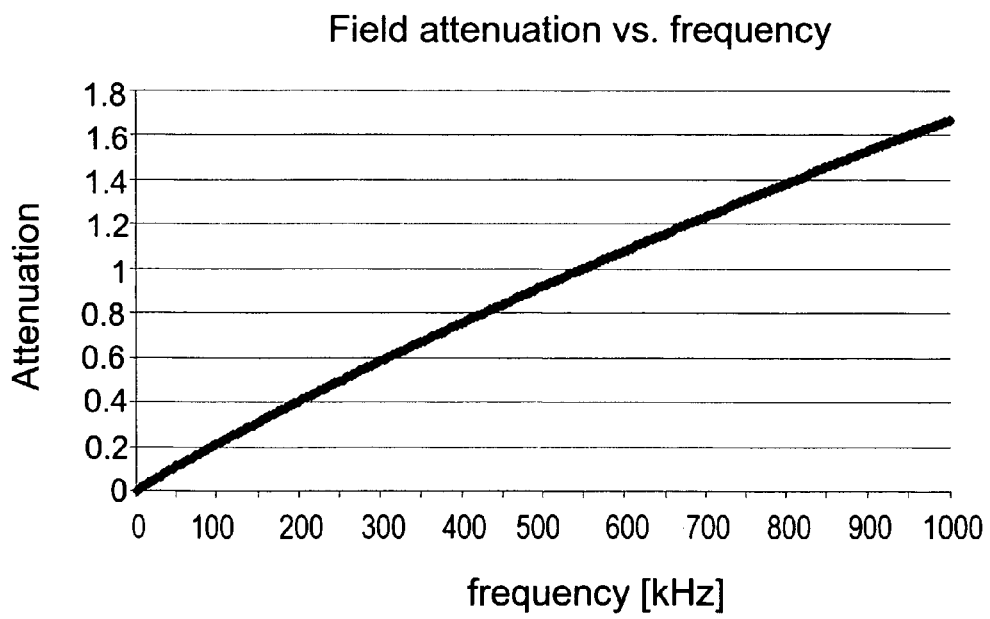
FIG. 14 is a graphic illustration of the dependence of the field attenuation upon frequency.

FIG. 14 graphically illustrates the dependence of the field attenuation upon frequency, for a tube thickness of 0.5 mm.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. An implant device for stimulating osteogenesis and osseointegration, comprising:
   a hollow annular housing member including a portion of said housing member sized and shaped for implantation into a bone;
   a pulsed current modulator mounted within said housing member producing a pulsed current, and
   an inductance coil mounted within said housing member, at least a portion of said coil extending apically into said implantable portion of said housing; said coil electrically connected to said pulsed current modulator to generate from said pulsed current an electromagnetic field of a predetermined flux density that penetrates, and propagates radially outwardly from, said housing member for a sufficiently large propagation distance to stimulate osteogenesis and osseointegration in said bone.

2. The implant device according to claim 1, wherein each pulse that is generated by said pulsed current modulator is of a sufficient duration to ensure that the total accumulated amount of energy associated with the electromagnetic field that is absorbed during a predetermined period by a region including said bone is greater than a predetermined amount.

3. The implant device according to claim 1, wherein the hollow housing member is engageable with an implanted root.

4. The implant device according to claim 3, which is a dental implant device, wherein the housing member includes a healing abutment engageable with an implanted root.

5. The implant device according to claim 3, wherein a wire extending from the coil portion mounted within the housing member is wound about an exterior surface of the root.

6. The implant device according to claim 3, wherein said housing member includes an external screw thread to engage said implanted root.

7. The implant device according to claim 3, wherein said housing member has an elongated hollow shape sized for at least partially insertion longitudinally into a bone implant.

8. The implant device according to claim 1, wherein the coil comprises a first portion disposed within a first housing member element and a second portion disposed within a second housing member element.

9. The implant device according to claim 8, wherein the coil includes a continuous coil that is formed with one or more windings.

10. The implant device according to claim 9, wherein the coil has a number of windings ranging from one to ten.

11. The implant device according to claim 8, wherein the first housing member element includes a coronal cap and the second housing member element includes a hollow screw, a coronal end of said hollow screw being threadedly engageable with said coronal cap and an apical end of said hollow screw being threadedly engageable with an implanted root.

12. The implant device according to claim 11, wherein the coil is a frame coil.

13. The implant device according to claim 12, wherein a first portion of each loop of the frame coil has a width substantially equal to the width of the first housing member element and a second portion of each winding of the frame coil has a width substantially equal to the width of the second housing member element.

14. The implant device according to claim 12, wherein the frame coil comprises a plurality of aligned loops.

15. The implant device according to claim 12, wherein the frame coil comprises two sections that are substantially mutually perpendicular.

16. The implant device according to claim 15, wherein each of the two sections is similarly configured.

17. The implant device according to claim 12, wherein the frame coil is an angularly distributed coil which is arranged such that all loops thereof have a common intersection point.

18. The implant device according to claim 17, wherein a maximum angular distribution of the loops is no greater than approximately 40 degrees.

19. The implant device according to claim 12, wherein the second portion of the coil extends apically substantially throughout the entire length of the second housing member element.

20. The implant device according to claim 12, wherein the coil is a frame coil which has an apical ring coil portion.

21. The implant device according to claim 8, further comprising a ferrite core insertable within the second housing member element.

22. The implant device according to claim 8, wherein the first coil portion surrounds the pulsed current modulator.

23. The implant device according to claim 8, further comprising a ferrite core insertable within the first housing member element.

24. The implant device according to claim 8, wherein the first portion of the coil and said second portion of the coil are connected to the pulsed current modulator in parallel.

25. The implant device according to claim 1, wherein an outer surface of the housing member is sufficiently electrically charged by means of the generated electromagnetic field to stimulate osseointegration with said bone.

26. The implant device according to claim 1, wherein said pulsed current modulator comprises at least one of an oscillator, timer circuitry, an internal power source, and a switch for terminating electrical connection between said power source and said timing circuitry.

27. The implant device according to claim 26, wherein the timing circuitry is adapted to modulate a pulsed waveform in continuous ongoing fashion according to a desired duty cycle.

28. The implant device according to claim 26, wherein said pulsed current modulator is adapted to modulate a sinusoidal pulsed waveform.

29. The implant device according to claim 26, wherein the power source includes a battery that has a sufficient capacity for powering said pulsed current modulator during an entire anticipated healing period of 4-12 weeks.

30. The implant device according to claim 26, wherein the pulsed current modulator further comprises an inverter for changing the radial direction of the generated electromagnetic field to an opposite direction.

31. The implant device according to claim 26, wherein the timing circuitry is adapted to modulate a pulsed waveform for a predetermined modulation duration.

32. The implant device according to claim 26, wherein the power source is selected from the group consisting of a piezo-electric device for generating piezoelectricity in response to applied masticatory forces, a capacitor, a dynamo, and an electro-kinetic actuator.

33. The implant device according to claim 1, wherein the generated electromagnetic field has a flux density ranging from 0.2 to 0.5 mT.

34. The implant device according to claim 1, wherein the frequency of the pulsed current ranges from 1 Hz to 1000 Hz.

35. The implant device according to claim 34, wherein the pulsed current has an average amplitude ranging from 1 to 2000 mA.

36. The implant device according to claim 1, wherein the pulsed current has a pulse duration ranging from 5 to 200 microseconds.

37. The implant device according to claim 1, which is an orthopedic implant device.

38. The implant device according to claim 1, wherein a wire extending from the coil portion mounted within the housing member is wound about an exterior surface of the housing member.

39. The implant device according to claim 1, wherein the hollow housing member is an implantable root.

40. The implant device according to claim 1, wherein the coil is a ring coil.

41. The implant device according to claim 40, wherein a first ring coil portion is disposed within a first housing member element, a second ring coil portion is disposed within a second housing member element, and one or two segments extend between said first and second ring coil portions.

42. The implant device according to claim 41, wherein the one or two segments that extends between said first and second ring coil portions is a frame coil portion.

43. The implant device according to claim 1, which is adapted to induce neural regeneration.

44. The implant device according to claim 1, which is a periodontal regeneration implant device.

45. The implant device according to claim 1, which is an orthodontic implant device.

46. The implant device according to claim 1, wherein said sufficiently large propagation distance comprises at least 2 mm.

47. The implant device according to claim 1, wherein the housing member comprises a hollow member, an apical end of said hollow member being engageable with an implanted root, and said coil is disposed within said hollow member.

48. The implant device according to claim 1, wherein said housing is sized and shaped for implantation into a jawbone, and wherein said sufficiently large propagation distance is at least 2 mm to stimulate osteogenesis and osseointegration, by means of said generated electromagnetic field, in a region of said jawbone in which said implant device is implanted and which is disposed radially outwardly from said housing member.

49. The implant device according to claim 48,
wherein said pulsed current modulator and said inductance coil are configured for generating a pulsating electromagnetic field of a predetermined flux density in said jawbone at a radially outward distance of at least 2 mm from said dental implant device to stimulate osteogenesis and osseointegration.

50. The implant device according to claim 49, wherein said flux density ranges from 0.2 mT to 0.5 mT.

51. The implant device according to claim 1, wherein said bone region in which osteogenesis and osseointegration is stimulated by said electromagnetic field is adjacent said implant, to improve bone to implant contact.

52. The implant device according to claim 1, wherein said bone region in which osteogenesis and osseointegration is stimulated by said electromagnetic field is located circumferentially around said implant.

53. The implant device of claim 1, wherein said inductance coil and a power source of said device are sized to fit into a bone implant.

54. The implant device of claim 1, wherein said inductance coil and a power source of said device are sized to fit into a dental implant.

55. The implant device according to claim 1, wherein said pulsed current modulator is adapted to modulate a substantially symmetrical pulsed waveform.

56. The implant device according to claim 1, wherein said portion of said housing has a hard outer surface.

57. The implant device according to claim 56, wherein said hard outer surface comprises metal.

58. The implant device according to claim 57, wherein said hard outer surface comprises titanium.

* * * * *